US007981160B1

(12) United States Patent
Serafin, Jr. et al.

(10) Patent No.: US 7,981,160 B1
(45) Date of Patent: Jul. 19, 2011

(54) MULTI-HOODED ENARTHRODIAL JOINT IMPLANT CUP AND SECUREMENT

(76) Inventors: Louis A. Serafin, Jr., Lakeport, MI (US); Floyd G. Goodman, Williamston, MI (US)

( * ) Notice: Subject to any disclaimer, the term of this patent is extended or adjusted under 35 U.S.C. 154(b) by 272 days.

(21) Appl. No.: 11/069,618

(22) Filed: Feb. 28, 2005

Related U.S. Application Data

(60) Provisional application No. 60/548,347, filed on Feb. 27, 2004.

(51) Int. Cl.
*A61F 2/34* (2006.01)

(52) U.S. Cl. .................................................... 623/22.25

(58) Field of Classification Search ..... 623/22.11–23.57
See application file for complete search history.

(56) References Cited

U.S. PATENT DOCUMENTS

| | | | | | |
|---|---|---|---|---|---|
| 3,584,318 | A | * | 6/1971 | Scales et al. | 623/23.43 |
| 3,698,017 | A | * | 10/1972 | Scales et al. | 623/22.24 |
| 4,135,517 | A | * | 1/1979 | Reale | 606/86 |
| 4,410,295 | A | * | 10/1983 | Ersoy et al. | 403/122 |
| 4,718,911 | A | * | 1/1988 | Kenna | 623/22.29 |
| 4,770,658 | A | * | 9/1988 | Geremakis | 623/22.19 |
| 4,936,855 | A | * | 6/1990 | Sherman | 623/22.2 |
| 5,019,105 | A | * | 5/1991 | Wiley | 623/22.29 |
| 5,507,828 | A | * | 4/1996 | Maumy et al. | 623/22.26 |
| 5,766,260 | A | * | 6/1998 | Whiteside | 623/22.27 |
| 5,938,702 | A | * | 8/1999 | Lopez et al. | 623/22.38 |
| 5,989,293 | A | * | 11/1999 | Cook et al. | 623/22.29 |
| 6,136,034 | A | | 10/2000 | Townley | |
| 6,162,256 | A | * | 12/2000 | Ostiguy et al. | 623/22.26 |
| 6,299,647 | B1 | | 10/2001 | Townley | 623/22.32 |
| 7,115,145 | B2 | * | 10/2006 | Richards | 623/22.29 |
| 7,169,186 | B2 | * | 1/2007 | Harris et al. | 623/22.29 |
| 2002/0058998 | A1 | * | 5/2002 | Church | 623/22.25 |
| 2003/0060890 | A1 | * | 3/2003 | Tarabishy | 623/22.12 |
| 2005/0004678 | A1 | | 1/2005 | Richards | |

FOREIGN PATENT DOCUMENTS

WO WO0209615 * 2/2002

OTHER PUBLICATIONS

Serafin, Jr., et al., U.S. Appl. No. 60/548,347, filed Feb. 27, 2004 A.D.
Zimmer, Inc., Epsilon (TM) Durasul (Reg. U.S. Pat. & Tm. Off.) Constrained Insert, Product Information & Surgical Technique.

* cited by examiner

*Primary Examiner* — David Isabella
*Assistant Examiner* — Ann Schillinger
(74) *Attorney, Agent, or Firm* — Christopher John Rudy

(57) ABSTRACT

Cup has an articular surface upon which a ball of a joint can articulate, and a margin generally about a hemisphere and at least two hoods that are marginally extended continuations of superior one-half or so of cup containment, a joint ball; and a securing member for resistance against outward displacement of the hood(s) so that the ball can be securely contained. An inwardly biased engagement tab can be is provided for hood brace(s), and perforation(s) or hole(s) can be present about the hood brace(s) and/or cover(s).

20 Claims, 3 Drawing Sheets

FIG. 6
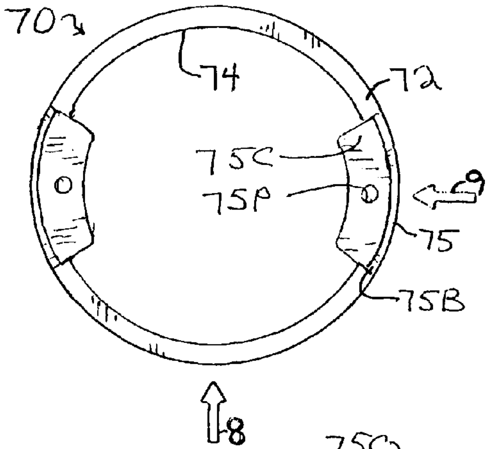
FIG. 7
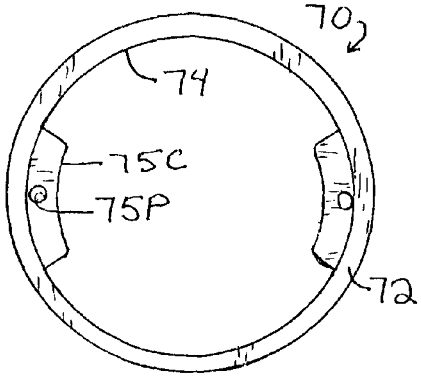
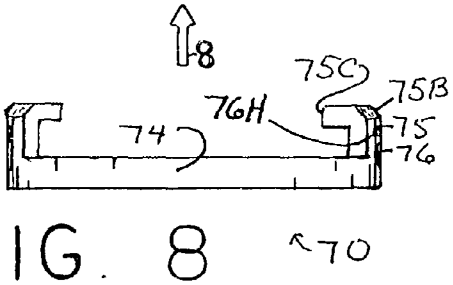
FIG. 8
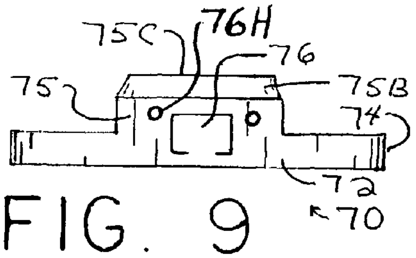
FIG. 9
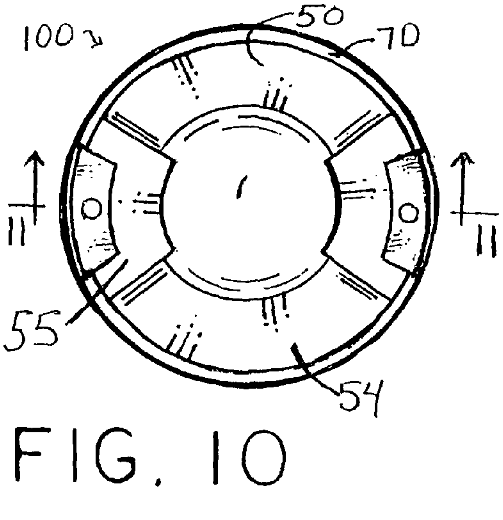
FIG. 10
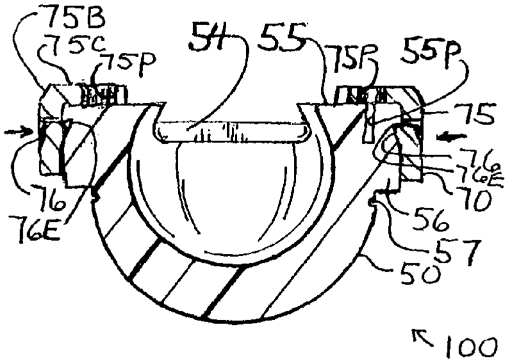
FIG. 11

MULTI-HOODED ENARTHRODIAL JOINT IMPLANT CUP AND SECUREMENT

CROSS-REFERENCE CLAIM OF PRIORITY

This claims benefits under 35 USC 119(e) of U.S. provisional patent application No. 60/548,347 filed on Feb. 27, 2004 A.D. The specification of that application is incorporated herein by reference in its entirety.

BACKGROUND TO THE INVENTION

I. Field and Purview

The present invention concerns a multi-hooded enarthrodial joint implant cup, which has a securing member; such cup ensemble in conjunction with a ball-containing counterpart joint implant component; and the securing member. The same can be for a hip.

II. Art and Problems

Dislocation of hip implants is a serious problem. Frequently the dislocation is debilitating to the patient, and can require a further surgery or implant to attempt to correct the problem.

In addressing this problem, various art is known.

U.S. Pat. No. 6,299,647 to Charles O. Townley discloses a snap-fitting, non-dislocating hip joint socket implant. This has a snap-fitted arrangement of the head-restraining marginal outlet of the acetabular component with posterior and anterior cut outs of the implant to avoid premature impingement against a prosthetic femoral neck, and a hood that is a marginally extended continuation of the superior one-half or so of the cup containment that is of a sufficient magnitude to reduce the overall dimension of the socket outlet to less than a hemisphere.

Sometime about 1997, William Harris discussed at Harvard University a double-hooded acetabular cup. This had opposing hoods that reduced the dimension of the socket outlet to less than a hemisphere. In conjunction with this cup, a certain retaining ring was also provided. Such a system is marketed by Zimmer, Inc. Compare, Zimmer, Inc., Epsilon™ Durasul (Reg. U.S. Pat. & Tm. Off.) Constrained Insert, Product Information and Surgical Technique.

Such art has its drawbacks. Dislocation still can and does occur, even with the known double hooded acetabular cups, and even the system with the ring mentioned above.

It would be desirable to improve the art. In particular, it would be desirable to provide an acetabular cup that is more resistant to dislocation.

DISCLOSURE OF THE INVENTION

In general, the present invention provides a multi-hooded enarthrodial joint implant cup ensemble comprising:

- a ball-receiving cup having an articular surface upon which a ball of a joint can articulate, and which has a margin generally about a hemisphere more or less and at least two hoods that are marginally extended continuations of superior one-half or so of cup containment of a sufficient magnitude to reduce an overall dimension of socket outlet to less than a hemisphere, which can embrace and contain the ball; and
- a securing member that provides for resistance against outward displacement of at least one of the at least two hoods so that the ball can be securely contained in the embrace of the at least two hoods.

The ensemble can further comprise a complimentary total joint implant component having the ball. The securement is of note.

The invention is useful in arthroplasty.

Significantly, by the invention, problems in the art are ameliorated if not overcome. In particular, total hip implants are made dramatically more secure by resistance to dislocation.

Numerous further advantages attend the invention.

The drawings form part of the specification hereof. With respect to the drawings, which are not necessarily drawn to scale, the following is briefly noted:

FIG. 6 is a "front" view of a securing member of the invention for an ensemble therewith, the same being embodied as a 6-4 ELI titanium alloy ring.

FIG. 7 is a "rear" view of the securing member of FIG. 6.

FIG. 8 is a "side" view of the securing member of FIG. 6, taken along arrow 8 in FIG. 6.

FIG. 9 is a "side" view of the securing member of FIG. 6, taken along arrow 9, which is normal to arrow 8 in FIG. 6.

FIG. 10 is a "top" view of an ensemble of the invention, which includes the cup of FIG. 1 and the securing ring of FIG. 6, without security enhancing fasteners such as screws depicted for clarity.

FIG. 11 is a sectional view of the ensemble of FIG. 10, taken along 11-11 in FIG. 10.

Figure 1:
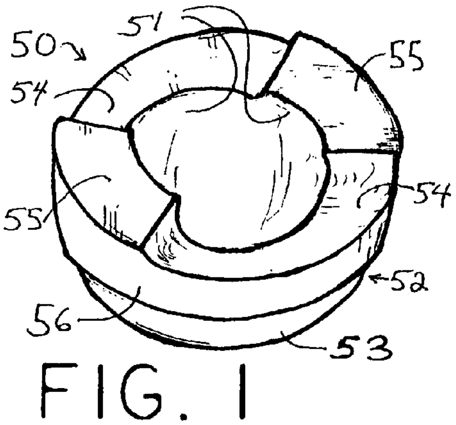
FIG. 1 is a perspective view of a multi-hooded enarthrodial joint implant cup of the invention for an ensemble therewith, the same being embodied as a double-hooded ultra high molecular weight polyethylene (UHMWPE) acetabular cup for a total conventional hip replacement implant.
Figure 2:
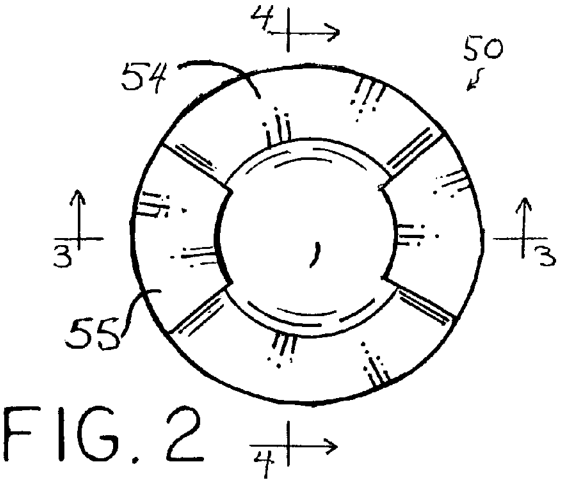
FIG. 2 is a "front" view of the cup of FIG. 1.
Figure 3:
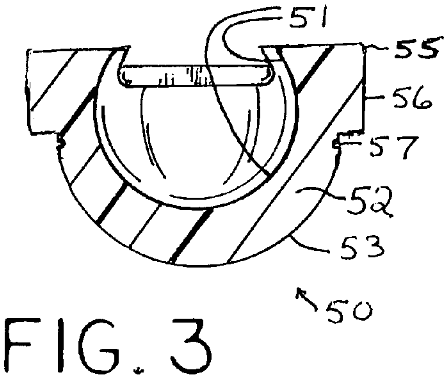
FIG. 3 is a sectional view of the cup of FIG. 1, taken along 3-3 of FIG. 2.
Figure 4:
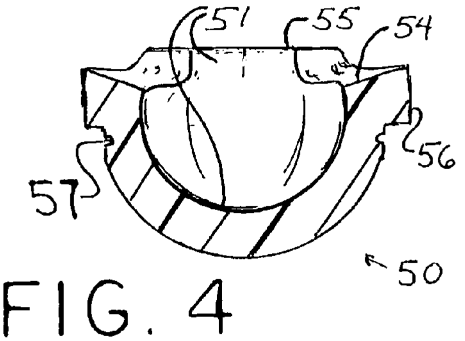
FIG. 4 is a sectional view of the cup of FIG. 1, taken along 4-4 of FIG. 2, which is normal to 3-3 of FIG. 2.

The invention can be further understood by the following additional detail, which may be read in view of the drawings. Such is to be taken in an illustrative and not necessarily limiting sense.

The principles of the invention can be applied to provide a multi-hooded enarthrodial joint implant cup ensemble, or parts thereof, for any suitable enarthrodial joint, to include the hip, shoulder, thumb or finger. The hip is preferred.

Any suitable material may be employed. Generally, materials are biocompatible. Thus, material for the cup may be selected from suitably resilient, tough materials that may include such plastics as polyurethanes or polyolefins, and so forth, for an example, a polyethylene. Material for the securing member, and any security enhancing fastener, may be selected from suitably rigid, strong materials that may include such plastics as nylons, polycarbonates or epoxies; such ceramics as aluminas and/or zirconias, especially magnesium oxide transformation toughened zirconia, e.g., stabilized by 3~3½% MgO; such metals or alloys as titanium, cobalt, stainless steel, titanium-vanadium-aluminum, cobalt-chrome, etc.

Additional component parts, if present, are made of suitable materials. For instance, a backing shell may be made of a suitable ceramic or metal, for example, 6-4 ELI titanium alloy; a corresponding ball-containing joint implant component, whether modular or of one piece, may be made of a suitable ceramic and/or metal, for example, a cobalt-chrome alloy or a cobalt-chrome alloy with a ceramic head.

The hoods of the cup embrace the ball of a joint greater than a hemisphere, in general, at least about their areas of contact with the ball. In other words, the hoods are marginally extended continuations of the superior one-half or so of the cup containment of a sufficient magnitude to reduce the overall dimension of the socket outlet to less than a hemisphere. The ball, be it natural or more typically artificial, is forced into the cup into the embrace of the hoods. After insertion of the ball into the hooded cup, the securing member is brought into position to secure the hoods from outward displacement, without which the ball would have an increased propensity to disengage from the embrace of the outwardly displaced hood (s) such as can occur with extended motion of the joint, and dislocate.

More than one hood is required in the practice of the present invention. Thus, for instance, two, three, four or more hoods may be employed, say, with two opposing hoods; with three hoods equidistant about the margin of the cup and margin segments and hoods having about the same arc lengths, or with hoods having less of an arc length than the margins such as from about ½ to ¾ of the arc length of the margins; with three hoods not equidistant about the margin and themselves having the same arc lengths, or with one having a larger arc length opposed by two with lesser arc lengths; with four hoods equidistant about the margin and margin segments and hoods having about the same arc lengths, or with hoods having less of an arc length than the margins; with four hoods about the margin, two of the hoods in a set opposing two of the hoods in another set with greater margins between the two sets of hoods than between each hood in a set, or in an asymmetric arrangement, and so forth. Preferably, the invention is embodied with a double-hooded cup.

As securement, the securing member provides for resistance against outward displacement one hood or more so that the ball can be securely contained in the embrace of at least two hoods. Preferably, the securing member thus secures at least two hoods. Advantageously, the securing member thus secures each of the hoods present with the cup. Any suitable form for the securing member may be employed. For example, it may take the form of a ring or a U-shaped or horseshoe-shaped member.

Additional parts or components may be present.

With respect to the drawings, multi-hooded enarthrodial joint implant cup ensemble 100 for receipt of joint ball 20 includes cup 50 and securing member 70.

The joint ball 20 made, for example, of cobalt-chrome alloy in accordance with ASTM F-799 standards, or, say, of a ceramic such as alumina or zirconia, typically is connected to a neck or stem. For instance, neck 21, made, for example, of the F-799 alloy, connects monolithically with a stem of the same material that is inserted into suitable bone stock, for example, the upper femur medullary canal, after surgical resection appropriate to the component and patient at hand has been carried out.

Figure 5:
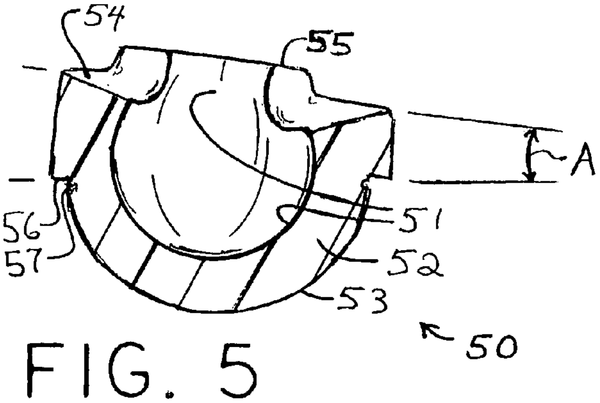
FIG. 5 is a sectional view of another multi-hooded enarthrodial joint implant cup of the invention for an ensemble therewith, the same being embodied as a double-hooded UHMWPE acetabular cup for a total conventional hip replacement implant, and having angular displacement of the margin and hoods. Compare, FIG. 4.
Figure 12:
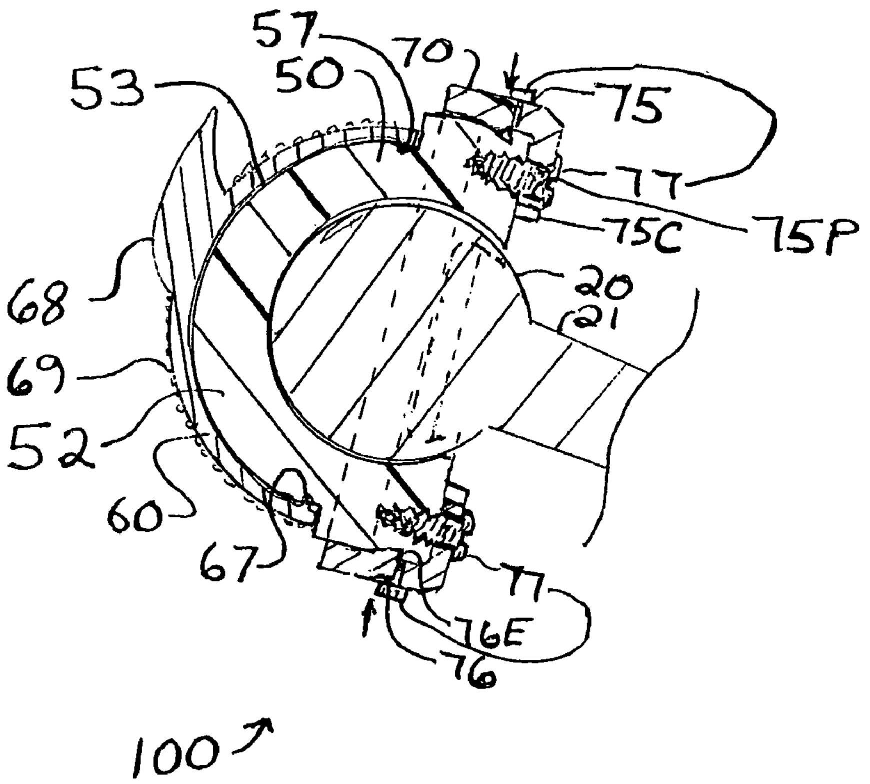
FIG. 12 is a sectional plan view of an ensemble such as that of FIG. 10 and as would be taken along 11-11 in FIG. 10, by which is embraced a ball of a corresponding implant, here, the ball of a femoral component for the total hip implant, with two security enhancing fasteners, and a backing shell, in place.

The cup 50 made, for example, of UHMWPE in accordance with ASTM F-648 standards, includes articular surface 51, body 52, back 53, margins 54, and hoods 55, one or more of which may be provided in advance or at the surgical site with pilot hole 55P. The cup 50 also includes circumferential lip 56, which, with the margins 54 and/or hoods 55, may be level (FIGS. 1-4, 10-12) or angled at angle "A," say, about from five to twenty degrees, say, about ten degrees (FIG. 5). The cup 50 also includes fastening aid 57, here, a circumferential groove for engagement with backing shell 60 made, for example, of 6-4 ELI titanium alloy in accordance with ASTM F-136 standards, which has complimentary fastening aid 67, here, a circumferential protrusion. The shell 60 also may have, among other things, optional cox-comb 68 for insertion into bone stock and/or roughened or porous coated surface 69 for interfacing with a resected bone surface and promoting bone ingrowth to stabilize the implant. Surgical cement such as polymethylmethacrylate may be employed.

The securing member 70 made, for example, of cobalt-chrome alloy to ASTM F-799 standards and generally in the shape of a ring, includes ring body 72 with marginal arcs 74 and hood braces 75 that include bevel 75B, cover 75C, and perforations 75P, which may take the form of holes. Engagement tabs 76 are biased inwardly, and have sharp edges 76E that engage the material of the cup 50 about the hood 55 slightly above the lip 56, so as to secure the ring 70 to the cup. In conjunction with or in lieu of the tabs 76 can be side holes 76H. Added fasteners 77 such as screws may be provided for further security, for example, which may be passed through the perforations and/or holes 75P, 76H.

To apply the invention in a surgical setting, especially as depicted in the present drawings, with the ball 20 and cup 50 disengaged, the securing member 70 is slipped over the ball 20 and neck 21 in a proper general orientation. Then the ball 20 is forced into the cup 50. Only then is the securing member 70 brought into position on the cup 50, and, if desired and/or equipped for it, any added security fasteners 77 are provided.

The present invention is thus provided. Various features, parts, subcombinations and combinations may be employed with or without reference to other features, parts, subcombinations or combinations of the invention, and numerous adaptations and modifications can be effected within its spirit, the literal claim scope of which is particularly pointed out as follows:

We claim:

1. A double-hooded enarthrodial joint implant cup ensemble comprising:

a ball-receiving cup having an articular surface upon which a ball of a joint can articulate, and which has a margin generally about a hemisphere, and two and only two generally opposing hoods that are marginally extended continuations of superior about one-half of cup containment of a sufficient magnitude to reduce an overall dimension of socket outlet to less than a hemisphere, which can embrace and contain the ball; and a securing member that provides for resistance against outward displacement of at least one of the two hoods so that the ball can be securely contained in the embrace of the two hoods;

wherein the securing member provides for resistance against outward displacement of both of the two hoods, and has a body in a form of a ring with two and only two braces, which generally oppose one another, connected to and projecting substantially perpendicularly away from a plane formed by the body, with both hood braces projecting on the same side of the plane; each of the hood braces is provided with a cover that extends inwardly toward the center of the ring from an end of the hood brace away from the ring; and an inwardly biased engagement tab is provided for at least one of the two hood braces, which can engage material of the cup about the hood so as to secure the ring to the cup, and which is present in the at least one of the two hood braces between the plane formed by the body in the form of the ring and the cover that extends inwardly toward the center of the ring from the end of the hood brace away from the ring.

2. The ensemble of claim 1, wherein the inwardly biased engagement tab is provided for each of the two hood braces, one per hood brace.

3. The ensemble of claim 2, which is for a total conventional hip replacement.

4. The ensemble of claim 2, wherein the cup is UHMWPE.

5. The ensemble of claim 2, wherein perforation(s) or hole(s) is(are) present about at least one of said covers and/or the at least one of the two hood braces, through which a fastener can pass and further secure the cup to the securing member.

6. The ensemble of claim 4, wherein perforation(s) or hole(s) is(are) present about at least one of said covers and/or the at least one of the two hood braces, through which a fastener can pass and further secure the cup to the securing member.

7. The ensemble of claim 3, wherein the cup is UHMWPE.

8. The ensemble of claim 3, wherein perforation(s) or hole(s) is(are) present about at least one of said covers and/or the at least one of the two hood braces, through which a fastener can pass and further secure the cup to the securing member.

9. The ensemble of claim 7, wherein perforation(s) or hole(s) is(are) present about at least one of said covers and/or the at least one of the two hood braces, through which a fastener can pass and further secure the cup to the securing member.

10. The ensemble of claim 1, which is for a total conventional hip replacement.

11. The ensemble of claim 10, wherein the cup is UHMWPE.

12. The ensemble of claim 10, wherein perforation(s) or hole(s) is(are) present about at least one of said covers and/or the at least one of the two hood braces, through which a fastener can pass and further secure the cup to the securing member.

13. The ensemble of claim 11, wherein perforation(s) or hole(s) is(are) present about at least one of said covers and/or the at least one of the two hood braces, through which a fastener can pass and further secure the cup to the securing member.

14. The ensemble of claim 1, wherein the cup is UHMWPE.

15. The ensemble of claim 14, wherein perforation(s) or hole(s) is(are) present about at least one of said covers and/or the at least one of the two hood braces, through which a fastener can pass and further secure the cup to the securing member.

16. The ensemble of claim 1, wherein perforation(s) or hole(s) is(are) present about at least one of said covers and/or the at least one of the two hood braces, through which a fastener can pass and further secure the cup to the securing member.

17. A securing member for a double-hooded enarthrodial joint implant cup ensemble that includes a ball-receiving cup having an articular surface upon which a ball of a joint can articulate, and which has a margin generally about a hemisphere, and two hoods that are marginally extended continuations of superior about one-half of cup containment of a sufficient magnitude to reduce an overall dimension of socket outlet to less than a hemisphere, which can embrace and contain the ball; which securing member comprises:

a body in a form of a ring; and two and only two hood braces connected to and projecting away from a plane formed by the body, with both hood braces projecting on the same side of the plane, wherein each of the hood braces is provided with a cover that extends inwardly toward the center of the ring from an end of the hood brace away from the ring, and the securing member can provide for resistance against outward displacement of the two hoods so that the ball can be securely contained in the embrace of the two hoods;

wherein an inwardly biased engagement tab is provided with at least one of said hood braces, which can engage material of the cup about the hood so as to secure the ring to the cup, and which is present in the at least one of the two hood braces between the plane formed by the body in the form of the ring and the cover that extends inwardly toward the center of the ring from the end of the hood brace away from the ring.

18. The securing member of claim 17, wherein the hood braces project substantially perpendicularly from the body, and oppose one another on the ring; and each of the two hood braces is provided with said inwardly biased engagement tab.

19. The securing member of claim 18, wherein perforation (s) or hole(s) is(are) present about at least one of the two hood braces and/or at least one of said covers, through which a fastener can pass and further secure the cup to the securing member.

20. The securing member of claim 17, wherein perforation (s) or hole(s) is(are) present about at least one of the two hood braces and/or at least one of said covers, through which a fastener can pass and further secure the cup to the securing member.

* * * * *